(12) United States Patent
Suon et al.

(10) Patent No.: US 6,726,621 B2
(45) Date of Patent: *Apr. 27, 2004

(54) RETRIEVAL DEVICES FOR VENA CAVA FILTER

(75) Inventors: Naroun Suon, Lawrence, MA (US); James Weldon, Roslindale, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 88 days.

This patent is subject to a terminal disclaimer.

(21) Appl. No.: 10/020,705

(22) Filed: Dec. 14, 2001

(65) Prior Publication Data

US 2002/0045918 A1 Apr. 18, 2002

Related U.S. Application Data

(63) Continuation of application No. 09/404,116, filed on Sep. 23, 1999, now Pat. No. 6,342,062.
(60) Provisional application No. 60/101,616, filed on Sep. 24, 1998.

(51) Int. Cl.$^7$ .................................................. A61F 2/02
(52) U.S. Cl. ...................................................... 600/200
(58) Field of Search ............................... 606/200, 113, 606/205, 206, 114, 127; 604/104

(56) References Cited

U.S. PATENT DOCUMENTS

| | | |
|---|---|---|
| 3,952,747 A | 4/1976 | Kimmell, Jr. |
| 4,425,908 A | 1/1984 | Simon |
| 4,643,184 A | 2/1987 | Mobin-Uddin |
| 4,832,055 A | 5/1989 | Palestrant ...................... 128/899 |
| 4,990,156 A | 2/1991 | Lefebvre ......................... 606/200 |
| 4,994,079 A | 2/1991 | Genese et al. .................. 606/206 |
| 5,108,406 A | 4/1992 | Lee ................................. 606/106 |
| 5,147,379 A | 9/1992 | Sabbaghian et al. .......... 606/206 |
| 5,171,233 A | 12/1992 | Amplatz et al. ............... 604/281 |
| 5,171,314 A | 12/1992 | Dulebohn ....................... 606/113 |
| 5,300,086 A | 4/1994 | Gory et al. ..................... 606/200 |
| 5,324,304 A | 6/1994 | Rasmussen ..................... 606/200 |
| 5,344,427 A | 9/1994 | Cottenceau et al. ........... 606/200 |
| 5,370,657 A | 12/1994 | Irie ................................. 606/200 |
| 5,383,887 A | 1/1995 | Nadal ............................. 606/200 |
| 5,413,586 A | 5/1995 | Dibie et al. .................... 606/200 |
| 5,415,630 A | 5/1995 | Gory et al. ....................... 604/53 |
| 5,634,942 A | 6/1997 | Chevillon et al. ............. 606/194 |
| 5,649,953 A | 7/1997 | Lefebvre ......................... 606/200 |
| 5,681,347 A | 10/1997 | Cathcart et al. ............... 606/200 |
| 5,944,728 A | 8/1999 | Bates ............................. 606/127 |
| 5,993,474 A | 11/1999 | Ouchi ............................. 606/206 |
| 6,251,122 B1 * | 6/2001 | Tsukernik ....................... 606/200 |
| 6,331,183 B1 * | 12/2001 | Suon .............................. 606/200 |
| 6,447,530 B1 * | 9/2002 | Ostrovsky et al. ............. 606/200 |

OTHER PUBLICATIONS

Greenfield et al., "Staging of Fixation and Retrievability of Greenfield Filters", *Journal of Vascular Surgery*, pp. 744–750, Nov. 1994.

Millward, "Temporary and Retrievable Inferior Vena Cava Filters: Current Status[1]", *JVIR*, vol. 9, No. 3, pp. 381–387, May–Jun. 1998.

"Gunther Tulip Vena Cava Filter Set", brochure, 10 pgs.

"Tricep™ Hooked–Prong Grasping Forceps", Microvasive Boston Scientific Corporation brochure, 1 pg.

* cited by examiner

*Primary Examiner*—Cary E. O'Connor
(74) *Attorney, Agent, or Firm*—Crompton, Seager & Tufte LLC

(57) ABSTRACT

A device for removing a thrombus filter from a blood vessel is disclosed. A device in accordance with the present invention includes a shaft having a proximal end, a distal end, and a lumen extending therethrough, a wire having a first end and a second end, the wire being partially disposed within the lumen of the shaft, a portion of the wire extending beyond the distal end of the shaft and forming a loop, and a portion of the wire extending beyond the proximal end of the shaft.

24 Claims, 3 Drawing Sheets

US 6,726,621 B2

RETRIEVAL DEVICES FOR VENA CAVA FILTER

CROSS REFERENCE TO RELATED APPLICATION

This is a continuation of Application Ser. No. 09/404,116 filed on Sep. 23, 1999, now U.S. Pat. No. 6,342,062, which claims the benefit of U.S. Provisional Application Ser. No. 60/101,616, filed Sep. 24, 1998.

BACKGROUND OF THE INVENTION

The present invention pertains to the field of intra vena cava filters. In particular, the present invention pertains to the retrieval of intra vena cava filters.

Intra vena cava filters are commonly implanted either temporarily or permanently in patients at risk for blood clotting.

SUMMARY OF THE INVENTION

The present invention pertains to an intra vena cava filter implantable temporarily or permanently, and methods for removal thereof. The filter includes struts having sharpened tips which engage the wall of the vein or inner surface of another organ to provide positional stability of the filter. The method in accordance with the present invention preferably includes the steps of further stabilizing the filter, compressing the struts and shielding the sharpened tips of the struts for subsequent removal of the filter.

DETAILED DESCRIPTION OF THE INVENTION

Figure 1:
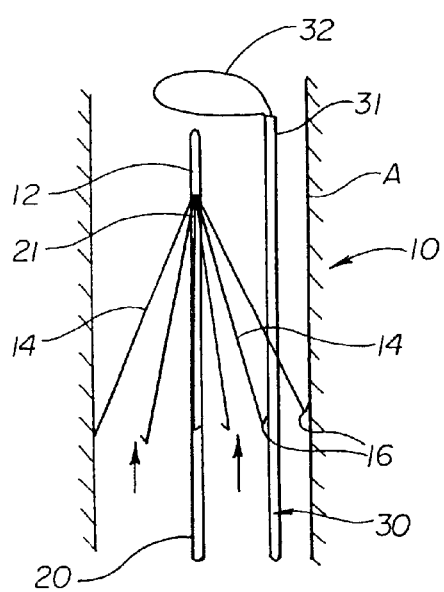
FIG. 1 is a view of an intra vena cava filter and a removal device disposed within a vessel.

Referring now to the drawings wherein like reference numerals refer to like elements throughout the several views, FIG. 1 is a side view of a filter 10 disposed within a vessel or vena cava A. Filter 10 includes a hub 12 from which extends a plurality of struts 14. Each strut preferably includes bends along its length to catch thrombus which flows through vessel A in the direction of the arrows. The end of each strut preferably includes a barb 16 for engagement with the vessel wall to stabilize filter 10 within vessel A. In particular, filter 10 can be a prior art filter such as the Greenfield™ filter made by Medi-Tech (Watertown, Mass.). Filter 10 can be placed within vessel A by way of a jugular vein access point or other intravascular route as known to those skilled in the art.

It is anticipated that the filter disclosed herein can be placed permanently in the vena cava or other organ, as well as being placed temporarily. The tools and methods for removing the filter disclosed herein would likely be used within several weeks after implantation of the filter prior to endothelial growth over a portion of the filter making removal substantially more difficult.

Also shown in FIG. 1 is a stabilizer 20. Stabilizer 20 includes a proximal end and a distal end 21. Stabilizer 20 can be advanced to filter 10 by way of a femoral vein access point. Stabilizer 20 is preferably made from a substantially rigid biocompatible material such as, for example, a stainless steel hypotube or steerable catheter.

Disposed adjacent filter 10 in FIG. 1 is a removal device 30. Removal device 30, like stabilizer 20, can be advanced to filter 10 by way of a femoral vein access point. Removal device 30 preferably includes an elongate shaft having a proximal end (not shown) and a distal end. Shaft 30 is preferably formed from a substantially rigid, biocompatible material such as a stainless steel hypotube. Extending from the distal end of shaft 31 is a wire loop 32. Wire loop 32 is preferably formed from a NiTi alloy such as Nitinol. The wire forming loop 32 preferably extends through shaft 31 to its proximal end such that a physician can draw loop 32 into shaft 31. The wire forming loop 32 is preferably heat set or mechanically biased to bend approximately perpendicularly to shaft 31, as shown in FIG. 1, as it is advanced from the distal end of shaft 31 in vessel A.

Figure 2:
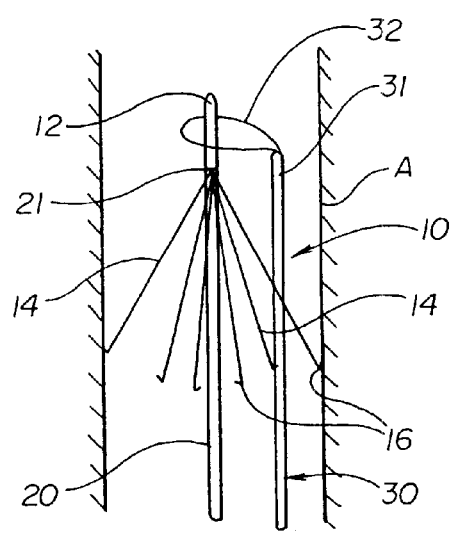
FIG. 2 is a view of the filter of FIG. 1 and the removal device in a subsequent position in the process of removal.
Figure 3:
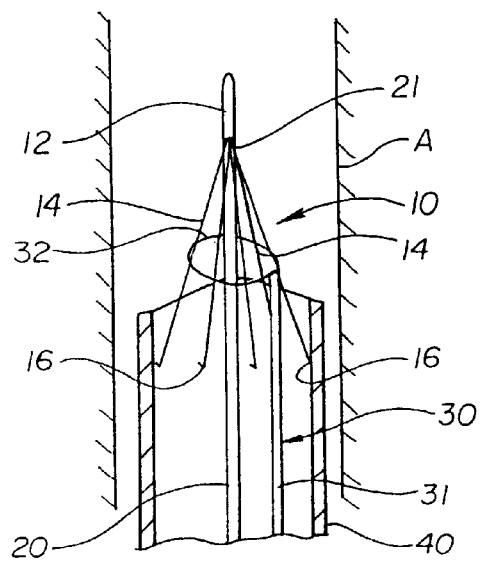
FIG. 3 is a view of the filter of FIG. 1 and the removal device in a position subsequent to that shown in FIG. 2 in the process of removal.

FIG. 2 is a view of the filter of FIG. 1, wherein loop 32 has been placed around filter 10 by pulling removal device 30 proximally. FIG. 3 is a view of filter 10 of FIG. 1, wherein device 30 has been pulled yet more proximally than shown in FIG. 2, relative to filter 10 and stabilizer 20. By pulling removal device 30 more proximally as shown in FIG. 3, struts 14 are compressed inwardly toward stabilizer 20 such that barbs 16 are withdrawn from the wall of vessel A.

Also shown in FIG. 3, in cross section, is a removal sheath 40. Sheath 40 can be formed of a biocompatible material in a manner similar to, for example, a guide catheter. Sheath 40 can be advanced to filter 10 by way of, for example, a femoral vein access point. As can be seen in FIG. 3, once struts 14 have been compressed sufficiently inward by removal device 30, filter 10 can be withdrawn into sheath 40, and subsequently removed from the patient.

Figure 4:
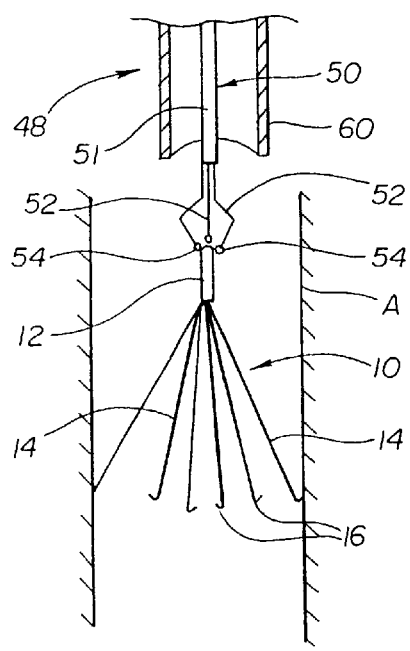
FIG. 4 is a view of the intra vena cava filter of FIG. 1 and an alternate embodiment of a removal device disposed within a vessel.

FIG. 4 is a view of the filter of FIG. 1. A removal device 48 is disposed above filter 10 in FIG. 4. Device 48 includes a stabilizer 50 and a catheter 60. Catheter 60 could be made in a manner similar to a guide catheter. Stabilizer 50 preferably includes a tubular shaft 51 having a proximal end (not shown) and a distal end. Preferably extending between the proximal end and the distal end are elongate members 52 having a distal end extending beyond the distal end of shaft 51. The distal end of members 52 are preferably bent to form a claw as shown. Atraumatic balls 54 can be disposed at the distal end of members 52. Removal device 48 can be placed in the position shown by way of, for example, a jugular vein access point.

Figure 5:
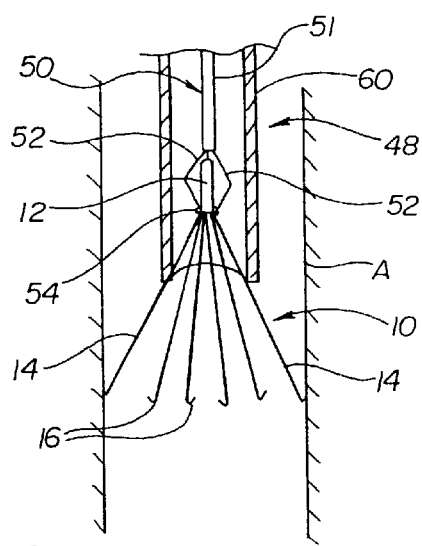
FIG. 5 is a view of the filter of FIG. 4 and the removal device in a subsequent position in the process of removal.

FIG. 5 is a view of the filter of FIG. 4 in which the claw portion of stabilizer 50 has been brought into contact with hub 12. Atraumatic balls 54 are shown engaging a portion of hub 12 to hold filter 10. The claw portion of device 50 can be closed to grasp hub 12 by advancing shaft 51 over members 52 to engage the claw portion forcing balls 54 toward each other. Once filter 10 is grasped by stabilizer 50, catheter 60 can be advanced into engagement with struts 14.

Figure 6:
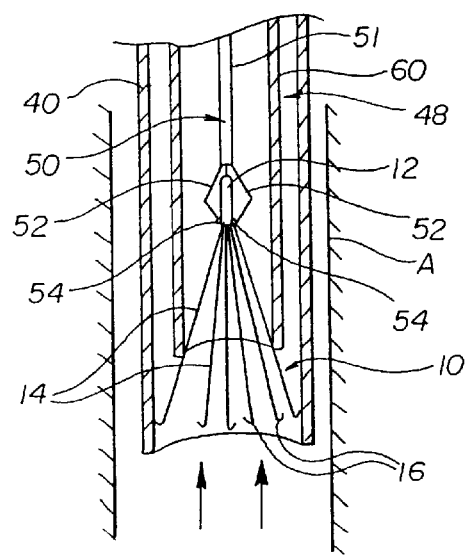
FIG. 6 is a view of the filter of FIG. 4 and the removal device in a position subsequent to that shown in FIG. 5 in the process of removal.

FIG. 6 shows the filter of FIG. 4, wherein catheter 60 has been advanced further than as shown in FIG. 5, to compress struts 14 inwardly and draw tips 16 away from the wall of vessel A. Sheath 40 has been advanced from, for example, a jugular vein access point over the entire filter 10. Sheath 40 shields the vessel wall from tips 16 during subsequent removal of filter 10 in the direction shown by the arrows.

Figure 7:
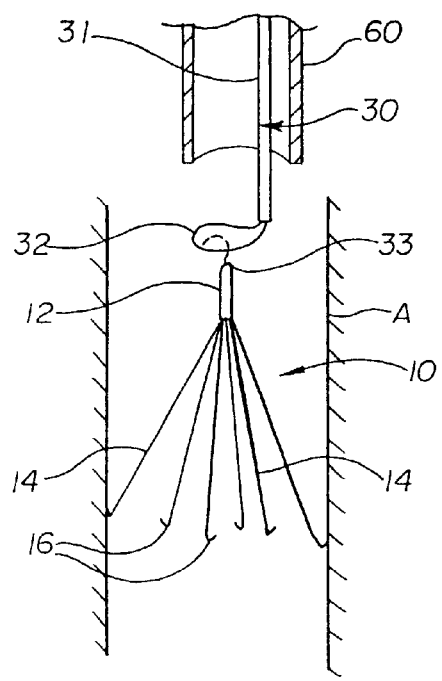
FIG. 7 is a view of the intra vena cava filter of FIG. 1 and yet an alternate embodiment of a removal device disposed within a vessel.

FIG. 7 is a view of the filter of FIG. 1 disposed in vena cava A. Positioned above filter 10 is removal device 30 disposed within catheter 60. Device 30 and catheter 60 are preferably advanced into this position by way of a jugular vein access point.

Figure 8:
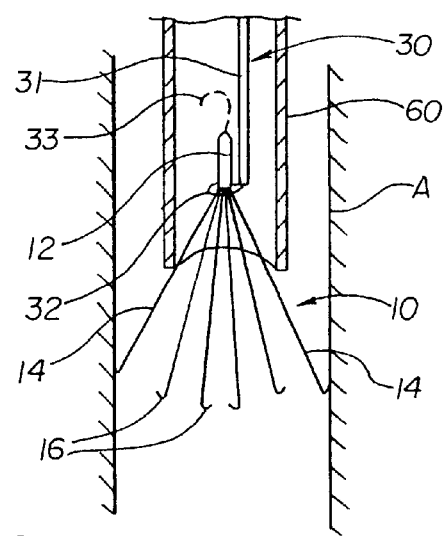
FIG. 8 is a view of the filter of FIG. 7 and the removal device in a subsequent position in the process of removal.

As shown in FIG. 8, loop 32 of device 30 has been placed around a portion of hub 12. Alternatively, hub 12 could include a hook 33 shown in phantom lines, to which loop 32 could be attached. The wire forming loop 32 has been drawn proximally into shaft 31 to tighten loop 32 around hub 12. Catheter 36 has been advanced distally to engage struts 14.

Figure 9:
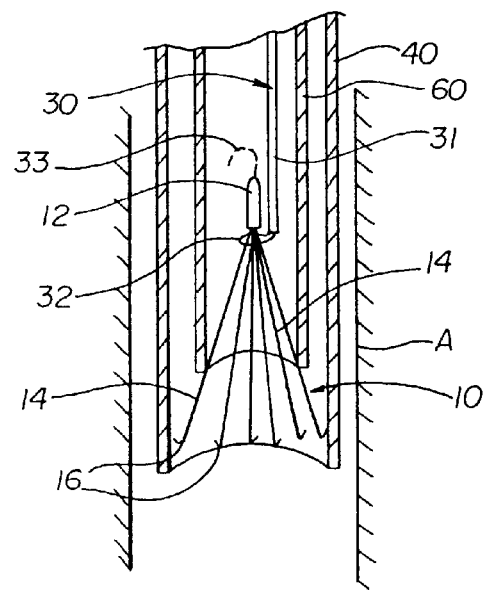
FIG. 9 is a view of the filter of FIG. 1 and the removal device in a position subsequent to that shown in FIG. 8 in the process of removal.

As shown in FIG. 9, catheter 60 has been advanced further relative to device 30 and filter 10 than as shown in FIG. 8. By advancing catheter 60 in this way, struts 14 have been compressed inwardly to disengage tips 16 from the wall of vessel A. Embodiments of the present invention have been envisioned, in which loop 30 is adapted to compress struts 14 inward and disengage tips 16 from the wall of vessel A. Methods in accordance with the present invention have been envisioned in which loop 32 is advanced distally to compress struts 14 inward and disengage tips 16 from the wall of vessel A. Sheath 40 is advanced distally as shown in FIG. 9 to cover filter 10 and shield the vessel wall from tip 16 as filter 10 is subsequently removed.

Numerous characteristics and advantages of the invention covered by this document have been set forth in the foregoing description. It will be understood, however, that this disclosure is, in many respects, only illustrative. Changes may be made in details, particularly in matters of shape, size and ordering of steps without exceeding the scope of the invention. The invention's scope is, of course, defined in the language in which the appended claims are expressed.

What is claimed is:

1. A medical device, comprising:
   a tubular sheath having a lumen;
   a tubular shaft disposed within the sheath, the shaft having a proximal end, a distal end, and a lumen extending therethrough;
   a retrieval member having a first portion disposed within the lumen of the shaft and a second portion adapted for being extended out of the distal end of the shaft;
   a filter including a hub having a plurality of arms extending therefrom;
   wherein the hub defines a narrow region of the filter and the plurality of arms define a wide region of the filter; and
   wherein the second portion of the retrieval member is adapted and configured to engage the filter over the hub of the filter.

2. The medical device in accordance with claim 1, wherein the filter arms each have a barb disposed at one end.

3. The medical device in accordance with claim 1, wherein the retrieval member includes a wire, and wherein the second portion includes a loop.

4. The medical device in accordance with claim 3, wherein the loop is adapted and configured to engage the filter hub.

5. The medical device in accordance with claim 3, wherein the filter hub includes a hook and the loop is adapted and configured to engage the hook.

6. The medical device in accordance with claim 3, wherein the shaft has a longitudinal axis and wherein the loop extends in a direction substantially perpendicular to the longitudinal axis of the shaft.

7. The medical device in accordance with claim 1, wherein the second portion of the retrieval member includes a plurality elongate members each including a plurality of bends such that distal portions of the elongate members form a claw.

8. The medical device in accordance with claim 7, wherein the claw is adapted and configured to engage the hub.

9. The medical device in accordance with claim 7, wherein the elongate members have atraumatic distal ends.

10. The medical device in accordance with claim 1, further comprising a stabilizer having a proximal end and a distal end, wherein the distal end is adapted to engage the filter.

11. The medical device in accordance with claim 1, further comprising a filter retrieval catheter adapted and configured for being passed over the sheath.

12. A thrombus filter assembly, comprising:
   a sheath having a proximal end, a distal end, and a lumen extending therethrough;
   a shaft disposed within the lumen of the sheath, the shaft having a proximal end, a distal end, and a lumen extending therethrough;
   a filter including a hub having a plurality of arms extending therefrom;
   means for retrieving the filter at least partially disposed within the lumen of the shaft, wherein means for retrieving the filter includes a wire disposed within the shaft, wherein the wire includes a loop portion; and
   a stabilizer disposed adjacent the filter, the stabilizer including a proximal end and a distal end, wherein the distal end is adapted to engage the filter.

13. The medical device in accordance with claim 12, wherein the filter arms each have a barb disposed at one end.

14. The medical device in accordance with claim 12, wherein the loop portion is adapted and configured to engage the filter hub.

15. The medical device in accordance with claim 12, wherein the filter hub includes a hook and the loop portion is adapted and configured to engage the hook.

16. The medical device in accordance with claim 12, wherein the shaft has a longitudinal axis and wherein the loop portion extends in a direction substantially perpendicular to the longitudinal axis of the shaft.

17. The medical device in accordance with claim 12, further comprising a filter retrieval catheter adapted and configured for being passed over the sheath.

18. A method of retrieving a filter from a blood vessel, comprising the steps of:
   advancing a retrieval catheter into a vascular region to an area adjacent a filter, the filter having a hub that defines a narrow region of the filter and a plurality of arms that define a wide region of the filter;
   advancing an elongate tubular member through the retrieval catheter, the tubular member having a distal end and a lumen;

advancing a retrieval member through the tubular member so that a first portion of the retrieval member extends out of the distal end of the tubular member;

disposing the first portion of the retrieval member over the hub of the filter to engage the filter; and retracting the retrieval member within the tubular member so as to alter the position of the filter and dispose a portion of the filter within the catheter.

19. The method in accordance with claim 18 wherein the retrieval member comprises a wire having a loop disposed at a distal end thereof, and wherein the step of disposing the first portion of the retrieval member over a portion of the filter to engage the filter includes disposing the loop over a portion of to filter.

20. The method in accordance with claim 19, wherein the filter includes a filter hub having a hook, and wherein the step of disposing the first portion of the retrieval member over a portion of the filter to engage to filter includes engaging the hook with the loop.

21. The method in accordance with claim 19, wherein the step of retracting the retrieval member within the tubular member so as to alter to position of the filter and dispose a portion of the filter within the catheter includes at least partially collapsing the filter by advancing the loop from the narrow region of the filter to a position over the widened region of the filter.

22. The method in accordance with claim 18, wherein the retrieval member includes a plurality elongate members at least partially disposed within the shaft, the elongate members each including one or more bends such that distal portions of the elongate members form a claw, and wherein the step of disposing the first portion of the retrieval member over a portion of the filter to engage the filter includes disposing the claw over a portion of the filter.

23. The method in accordance with claim 18, wherein the step of retracting the retrieval member within the tubular member so as to alter the position of the filter and dispose a portion of the filter within the catheter includes the step of at least partially collapsing the filter within the catheter.

24. The method in accordance with claim 23, further comprising the step of advancing a second tubular member over the catheter so as to dispose the filter within the second tubular member so that at least a portion of the filter is in direct contact with the second tubular member.

* * * * *